United States Patent [19]

Weiderrich

[11] 4,293,966
[45] Oct. 13, 1981

[54] LEAFCUTTER BEE LARVAE EXTRACTING METHOD AND DEVICE

[75] Inventor: LeRoy J. Weiderrich, North Havre, Mont.

[73] Assignee: Pollination Technics, Inc., Havre, Mont.

[21] Appl. No.: 82,991

[22] Filed: Oct. 9, 1979

[51] Int. Cl.³ .............................................. A01K 51/00
[52] U.S. Cl. ................................................. 6/12 R
[58] Field of Search .............. 6/11, 12 R, 12 F, 12 M, 6/12 A; 15/3.16, 3.17, 3.19

[56] References Cited

U.S. PATENT DOCUMENTS

| | | | |
|---|---|---|---|
| 1,881,354 | 10/1932 | Everett | 15/93 R |
| 2,580,397 | 1/1952 | Bogenschutz | 6/12 A |
| 3,290,705 | 12/1966 | Harrison | 6/12 A |
| 3,337,898 | 8/1967 | Schmid et al. | 15/404 |
| 3,735,433 | 5/1973 | Smith | 6/12 A |
| 3,889,306 | 6/1975 | Geertson | 6/12 M |
| 3,965,509 | 6/1976 | Barber | 6/12 A |
| 4,207,637 | 6/1980 | Niebur | 6/1 |

Primary Examiner—Paul J. Hirsch
Assistant Examiner—Robert P. Swiatek
Attorney, Agent, or Firm—Dowrey & Cross

[57] ABSTRACT

A method and apparatus for cleaning bee culture nests or hives of the spirally wound type, which are formed by spirally wound strips of corrugated and separator material. Bee larvae are removed and the nests cleaned by unwinding and separating the corrugated and separator strips, mechanically cleaning the strips and rewinding them to form a hive for reuse. The mechanical cleaning of the corrugated strip is accomplished by a plurality of fingers arranged to move through the flutes on each side thereof to remove the bee larvae. Scrapers contact both sides of the separator strip to remove the remaining adherent nesting material or "debris".

19 Claims, 8 Drawing Figures

U.S. Patent  Oct. 13, 1981  Sheet 3 of 4  4,293,966
FIG. 4
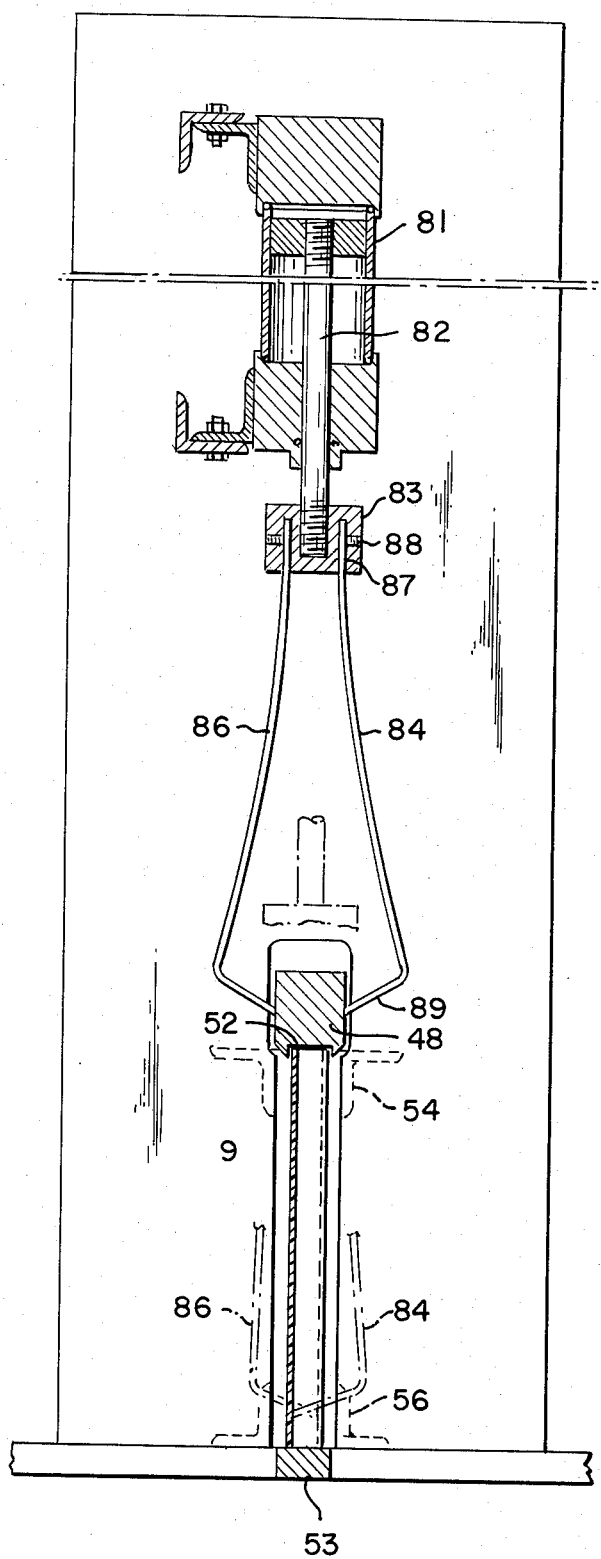
FIG. 5
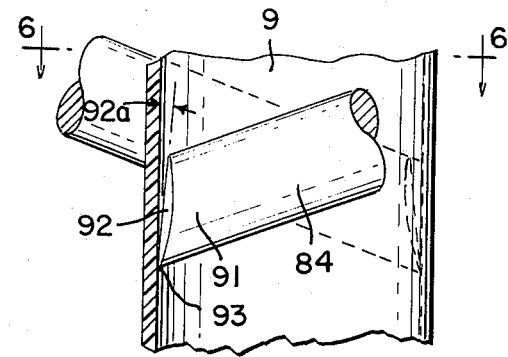
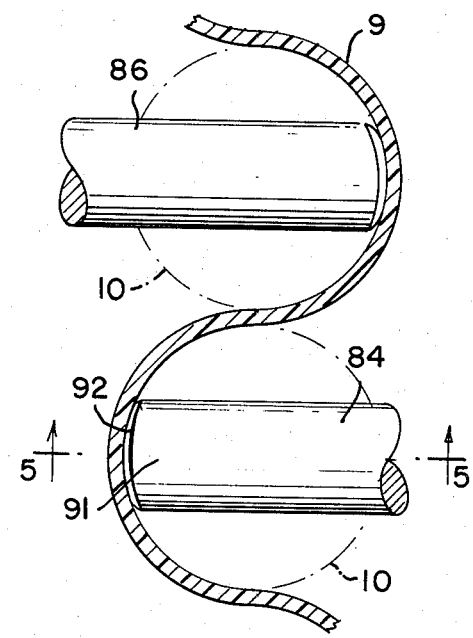
FIG. 6

FIG. 7
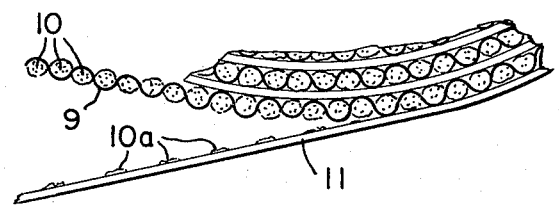
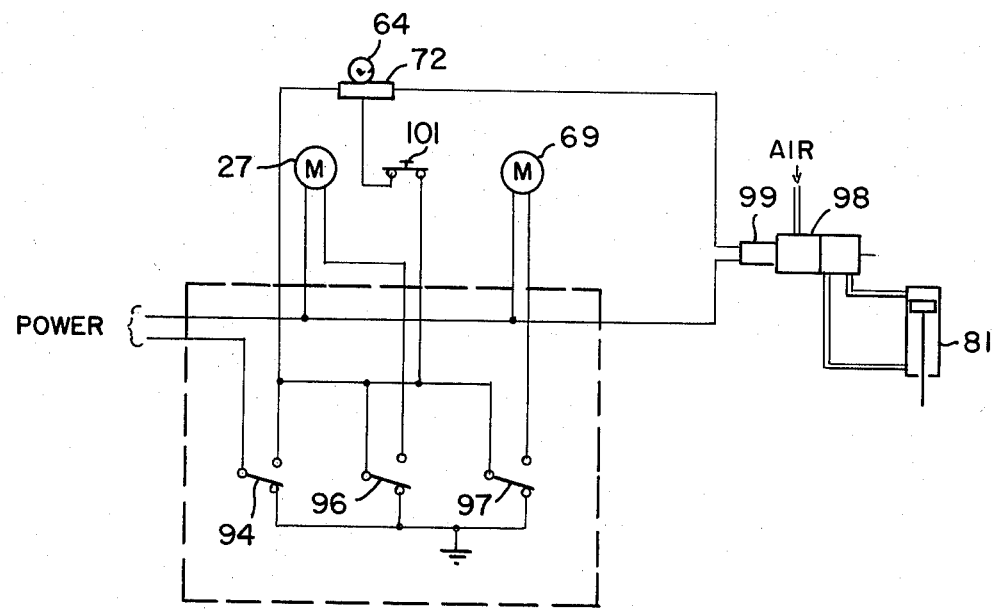
FIG. 8

LEAFCUTTER BEE LARVAE EXTRACTING METHOD AND DEVICE

FIELD OF THE INVENTION

The present invention relates to the handling of bee culture nests or hives and more particularly the processing and removal of bee larvae from such hives or nests of the spirally wound type. The invention has particular application to the nesting and processing of larvae of the leafcutter bee (Megachile rotundata) commonly used in alfalfa pollination.

DESCRIPTION OF THE PRIOR ART AND BACKGROUND OF THE INVENTION

In large sections of the United States and other parts of the world the land is uniquely suitable for the growth of alfalfa as a stock feed. Irrigation projects have increased the amount of land available for the cultivation of alfalfa and, as a result, there is a continuing demand for alfalfa seed. Since alfalfa is an annual and must be reseeded each year for continuing production, a problem in the expansion of alfalfa production has been a lack of sufficiently large supplies of seed. Under current technology, production of alfalfa seed has been somewhat of a gamble for the farmer since, along with problems of water, soil, weather and insects that harass all farming endeavors, there is the additional problem that alfalfa is not wind pollinated as are many other crops. Attempts have been made to pollinate alfalfa by mechanical devices such as dragging chains across the fields. These approaches have not achieved any appreciable commercial success.

Search for a means of pollination of alfalfa has thus turned largely to the different species of bees. In the states of California and Utah, for instance, some success has been obtained by the use of honey bees for pollination in the production of alfalfa seed but this approach has been generally accepted. In several of the western United States the akali bee (Nomia melanderi), a native species which nests in soil that is firm and moist and relatively free of vegetation, is also used for pollination. Although the alkali bee has not been domesticated, by encouraging propagation, the yield of alfalfa seed can be significantly increased. Reliance must be had on nature, to a large degree, for supply and upkeep of the quantity of bees needed for pollination.

A second bee species, the leafcutter bee (Megachile rotundata), is assuming ever greater importance for pollination of alfalfa crops in the western United States and Canada. This species, originally a native of middle eastern Europe, will nest in holes left by boring insects, typically in rotting wood. It will, however, readily accept artificial nests and is quite gregarious, several bees nesting close together, thus widespread domestication has occurred.

Several types of nests for leafcutter bees have been developed, perhaps the simplest being a wooden block with approximately 3/16th inch diameter holes drilled into its face to provide nesting holes. The blocks are placed in shelters on the edges of the alfalfa fields during the nesting season. While the raw-material of the nesting block is relatively inexpensive, the labor involved in drilling large numbers of holes and the practice of discarding the block at the end of one season due to the difficulty in cleaning renders them relatively unsatisfactory for most growers. Another very inexpensive form of leafcutter bee nest may be made simply by using a box of drinking straws of the appropriate length, open at one end exposing the interiors of the straws. Although the straws are inexpensive and may be conveniently disposed of at the end of the season, eliminating cleaning problems, the high vulnerability to parasites, to the sacrifice of the bee larvae, presents a serious problem.

With the increase in leafcutter bee populations there has been a corresponding increase in the numbers and effects of parasites. In excess of thirty parasites and other natural enemies have been identified, the most common and destructive parasite being a wasp (*Monodontomerus obscurus*). This wasp lays eggs in the nests which hatch into larvae that devour the bee larvae. Among the other enemies of the leafcutter bee are so called "nest destroyers" which are stored-products pests which simply destroy bee larvae in the process of feeding through the nest materials. The most common of these are the carpet beetle (*Trogoderma glabrum*), the red flower beetle (*Tribolium castaneum*), the checkered flower beetle (*Trichodes ornatus*) and the dried-fruit moth (*Vitula edmandsae serratilineela*). The presence of these pests and their larvae requires thorough cleaning and sterilization of the bees' nests at the end of each season to control their spread and to maintain bee population. These conditions have led to the need for the development of new forms of nesting structures which are more nearly parasite proof and/or cleanable and reusable. The economics of maintaining large numbers of nests has also become a prime factor in the alfalfa seed growing industry.

The first type of truly reusable and cleanable nest or hive developed comprised a plurality of wooden boards having parallel grooves on both faces. The boards are stacked and held in a frame with the aligned grooves in the mating faces forming nesting holes. At the end of each season the grooved boards are removed from the frames and cleaned and sterilized. Certain problems arise with the use of wooden boards, however, due to the porous nature of the material and the difficulty in obtaining thorough cleaning. In recent years use of wooden boards has given way to more expensive polystyrene boards in attempts to solve the cleaning problems. In any case the advent of the grooved board nest has made it possible to remove the larvae before they are mature and place them in incubators. By use of optimum temperature incubators the time required for maturity of the bees is lessened and a greater ultimate number of bees may be produced from a given number of starting bees. Additionally, the complete domestication and control of the life cycle of the leafcutter bee allows greater control of parasitic insects and other natural enemies such as birds, rodents and the like. The major problem remained, however, in devising inexpensive and efficient means for removing bee larvae from the nests without injuring the larvae or damaging the nests.

Originally the bee larvae had to be scraped from the individual grooves in the boards by hand using a knife or other instrument which was a time consuming and expensive task. Early efforts to mechanize the cleaning process involved such apparatus as devices for holding the boards and moving them past fixed wooden teeth arranged to scrape and clean the grooves. More recently mechanical devices have been designed for the purpose of separating the grooved boards, scraping the larvae from the grooves and collecting and separating the larvae from nest debris. One such known device is disclosed in the Theodore C. Barber, U.S. Pat. No. 3,965,509.

An improved spirally wound type of nest has come into existence in the past few years which offers many advantages over prior devices in terms of economy, ease of handling and improved protection against parasites. Originally the nest or hive consisted essentially of an approximately 4 inch wide spirally wound strip of corrugated paper of the type used in cardboard box making. The flutes of the corrugated strip, when wound on itself in spiral fashion, provide a multitude of nesting holes for the leafcutter bees. Although the first such nests were made of paper and were discarded at the end of each season, improvements have led to the use of ABS plastic or other polymeric material for the corrugated strip and a separator strip is now wound with the corrugated strip to separate the layers of corrugations. The preferred material for the separator strip is a flexible foam material which prevents migration of parasites between the layers of the corrugated strip. The walls of the corrugated strip act to prevent such parasites from boring between the walls of the larvae cells. To process the bee larvae, the spiral nest must be unwound, the larvae extracted from the flutes on both sides of the corrugated strip, both strips cleaned and subsequently rewound for reuse. This process, of course, has given rise to the need for an apparatus and method hitherto unknown in the art for carrying out these steps. The present invention provides a novel apparatus and method for accomplishing these steps in a highly efficient and economical manner.

SUMMARY OF THE INVENTION

The present invention provides a method and apparatus for efficiently extracting bee larvae "cells" from the flutes of the corrugated strip of a spirally wound hive. In the process, both the corrugated strip and a separator strip are mechanically scraped and cleaned. The hive may be unwound, cleaned and rewound ready for reuse in a matter of minutes. In the process of cleaning, the strips are initially separated as they are unwound and material removed from both sides of each strip as they are advanced incrementally through the extractor portion of the device. The larvae cells, along with all nest materials, are collected for further processing. The cleaned strips are brought back into face-to-face contact and rewound to form the spiral hive. With the present method and apparatus, larvae cells are removed and collected at a rate and with an efficiency and incidence of damage to both hive and larvae cell hitherto unknown in the art.

BRIEF DESCRIPTION OF THE DRAWINGS

FIG. 4 is a cross section view taken along lines 4—4 of FIG. 1 with certain parts removed to illustrate the operation of the larvae extracting fingers;

FIG. 5 is a detailed side elevational view showing the positioning of a finger relative to a flute of the corrugated strip during the cleaning operation;

FIG. 6 is a detailed plan view showing the positioning of two opposed fingers relative to adjacent flutes of the corrugated strip;

FIG. 7 is a detailed plan view of a peripheral section of the hive during the unwinding operation; and FIG. 8 is a schematic of the electrical control system for the extractor.

DETAILED DESCRIPTION OF THE DRAWINGS

Figure 1:
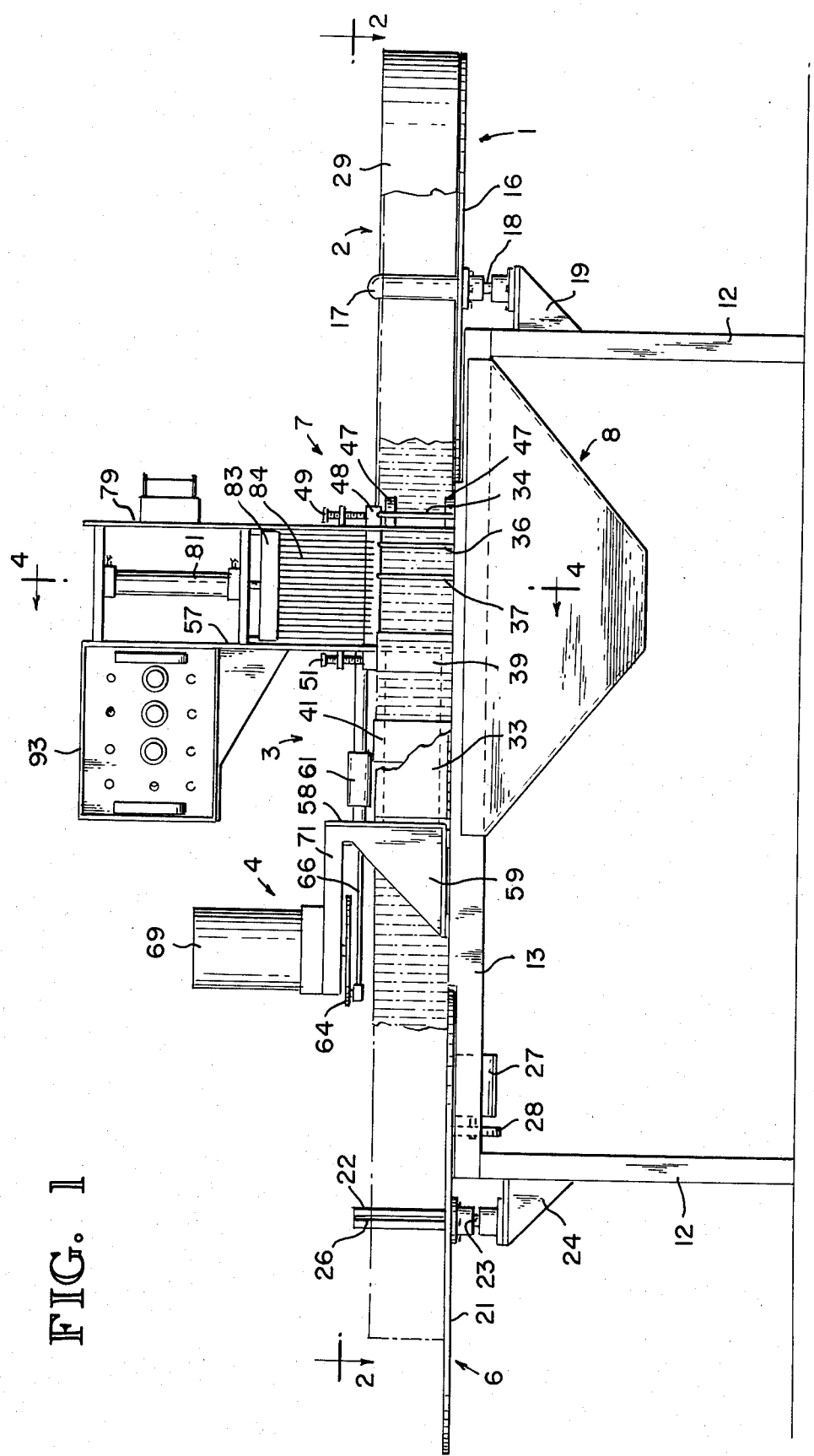
FIG. 1 is a side elevational view of the larvae extractor.

Referring now to the drawings wherein like reference numerals indicate identical parts in the various views, the larvae extractor includes generally an unloading reel 1 for holding a spirally wound corrugated-strip hive 2 presently to be described in detail. The spirally wound corrugated strip is pulled from the reel 1 by means of an advance or feed mechanism, indicated generally at 3, driven by the motor and cam assembly 4. The corrugated strip and the separator strip are removed after cleaning by the driven take-up reel 6. The larvae and nest debris are removed from the corrugated strip and separator strip respectively by the extractor assembly indicated generally at 7 as they are pulled from the reel 1. A discharge collector 8 is located beneath the extractor assembly for collecting the larvae and nest material cleaned from the strips.

Figure 2:
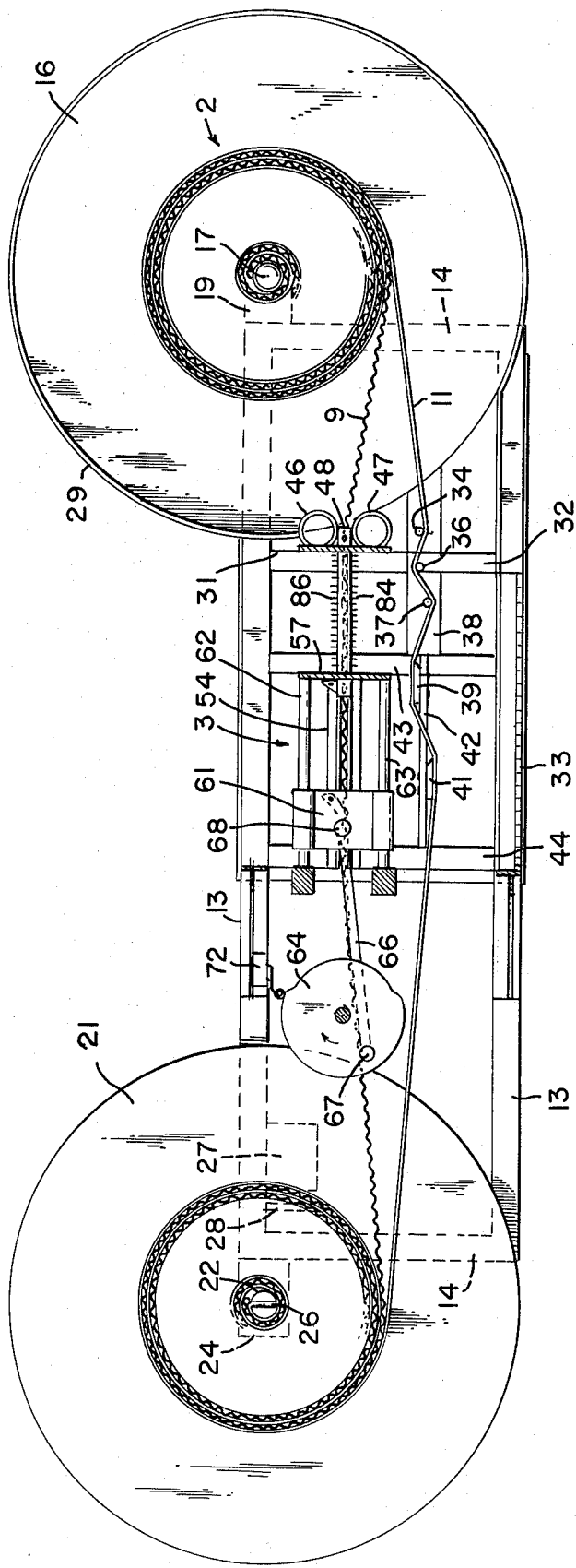
FIG. 2 is a top plan view of the extractor taken along lines 2—2 of FIG. 1.

Referring to FIGS. 2 and 7, the bee hive associated with the present invention comprises a corrugated strip 9 and a separator or divider strip 11. The details of construction of the hive itself form no part of the present invention and are the subject matter of my copending U.S. patent application filed concurrently herewith. The hive will be described herein only to the extent necessary for a complete understanding of the larvae extractor and method of the present invention and reliance for an understanding of the hive may be had on the disclosure of my copending application incorporated herein by reference. Generally, the corrugated strip may be made from ABS plastic or other polymeric material and may be approximately 0.015 inches in thickness so as to be impregnable to wasps and other parasites. The separator or divider strip may be constructed from any flexible foam material, usually plastic such as polyfoam and is thick enough so as to prevent parasites from reaching the bee larvae located in the flutes of the corrugated strip. In practice, the foam material may be approximately 3/16 inch in thickness and the flutes of the corrugated strip may have a radius of approximately ¼ inches. As aforementioned, for optimum male-female ratio of larvae production, the corrugated and separator strips should be approximately four inches in width.

As illustrated most clearly in FIG. 7, as the strips 9 and 11 are unreeled, each flute of the corrugated strip 9 will contain a number of larvae (cells) 10 along with a quantity of nesting material. A certain amount of nesting material or "debris" 10a will adhere to the foam separator strip 11.

Referring to FIGS. 1 and 2, a support structure is provided which includes the four upright legs 12 and a rectangular horizontal frame comprising the side rails 13 and end rails 14. The frame may be constructed from angle iron or the like, welded or otherwise rigidly connected in any conventional manner. The support structure serves to support the unloading and take-up reels, the extractor assembly and the larvae discharge collector 8 as previously discussed. The collector 8 may be of any known design and is connected to the side rails 13 directly beneath the advance mechanism and extractor assembly. The details of the collector form no part of the present invention and may include such apparatus as tumblers or separators or the like for further processing the larvae cells and other material removed from the hive.

The unloading reel 1 comprises a circular turntable 16 fixed to an upstanding center bearing shaft 17 mounted for free rotation on the shaft 18 carried by the bracket 19. The bracket may be welded or otherwise fixed to any part of the support frame as shown so as to position the hive 2 for unreeling. The hive, of course, is placed over the shaft 17 and rests on the turntable 16 so that the strips 9 and 11 may be pulled freely by the advance mechanism to be described.

The take-up reel 6 is mounted at the opposite end of the support frame and may be identical in structure to the unloading reel 1. The reel 6 comprises a take-up turntable 21 fixed to the upstanding center shaft 22 mounted for free rotation on bearing shaft 23 carried by bracket 24. The shaft 22, in case of the take-up turntable, will also be provided with a verticle slot 26 for initially holding the free ends of the strips 9 and 11 to start the rewinding of the cleaned hive. It would be practical, of course, to provide both shafts 17 and 22 with such slots in order to have them interchangeable if desired.

In order to provide a non positive drive for the take-up turntable 21 a gear reduction motor 27 is mounted to side rail 13 as illustrated in FIG. 2 and is provided with a friction drive wheel 28 which contacts the bottom side of the turntable 21. The motor 27 is a constantly operating motor and, with the slipping friction engagement of the drive wheel 28, a constant take-up pull or tension will be maintained on the strips 9 and 11 as they are advanced in stepping motion by the advance mechanism 3 presently to be described in detail.

As best shown in FIG. 2, an upstanding protective skirt or guard 29 extends from the area adjacent the advance mechanism and extractor fingers at the front of the device, about the unloading turntable 16, and terminates adjacent the infeed guide for the corrugated strip on the back side of the machine. The guard or skirt may be attached in any desired fashion to the side rails 13 and terminates at the post 31 fixed to the cross frame member 32. The guard may be provided with an access door portion 33 hinged to the frame 13 in any convenient manner (not shown) so as to permit access to the advance mechanism and the extractor fingers.

Figure 3:
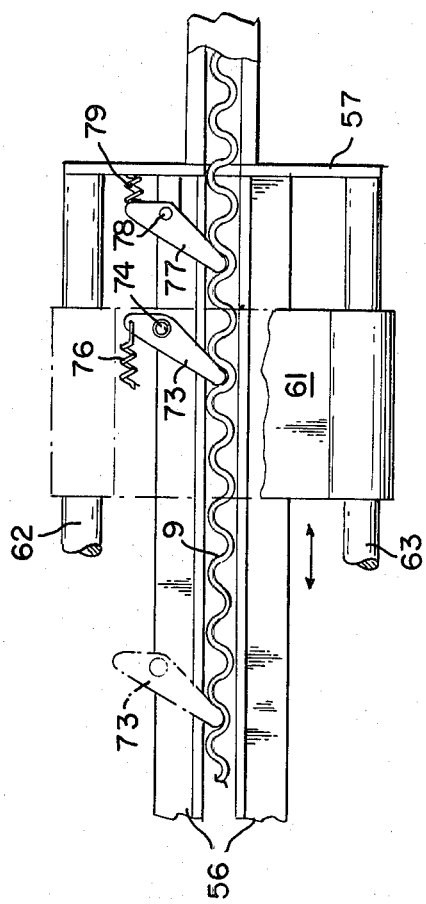
FIG. 3 is a detailed view showing the operation of the corrugated strip advance mechanism.

Referring to FIGS. 2 and 3, the advancing mechanism operates only on the corrugated strip 9 which takes a path through the device entirely separate from that of the separator strip 11. The strip 11 is tensioned only by the pull of the take-up reel driven by the slipping friction drive. Thus strip 11 is constantly tensioned or pulled but is allowed to move only in conjunction with the stepping or incremental movement of the corrugated strip 9.

As the strip 11 is unreeled it is drawn past three upright guides 34, 36 and 37 mounted on a longitudinal frame member 38. The guides direct the strip into position to be contacted by first upstanding scraper blade 39 for scraping and cleaning one side of the strip and a second scraper blade 41 located for contact and cleaning of the opposite side of the strip. The blades 39 and 41 are bolted or otherwise fixed to the longitudinal frame member 42 which extends between the cross frame members 43 and 44. The material scraped from the separator strip usually comprises nest material or debris which falls into the collector 8.

The corrugated strip 9 is guided beneath the extractor assembly and through the advance mechanism by means of first and second pairs of infeed guide rings 46 and 47 respectively. These guide rings are positioned to lightly contact the upper and lower opposite edge surfaces of the corrugated strip so as to guide the upper edge of the strip beneath a grooved guide bar 48. Referring to FIG. 1, the guide bar 48 is vertically adjustably mounted by the screws 49 and 51 mounted on the framework of the extractor assembly presently to be described. Thus, as illustrated in FIG. 4, as the corrugated strip travels beneath the extractor assembly, the top edge thereof moves within the groove 52 in the bottom face of the bar 48 and the bottom edge is supported on a suitable support bar 53. As the corrugated strip 9 travels to the advance mechanism it is maintained in position by upper and lower sets of guide bars 54 and 56 respectively. These guide bars extend between vertical plate 57, forming part of the extractor assembly, and the plate 58 which forms part of the support structure for the cam motor unit 4. The plate 58 may be rigidly mounted by the gussets 59 fixed to the side rails 13 in any desired manner. As seen most clearly in FIG. 2, the strip 9 is thus caused to move from the extractor assembly past the advance mechanism in straight line fashion and from there to the wind-up point on the turntable 21 where it is again brought into face-to-face contact with the separator strip 11.

The advance mechanism for moving the corrugated strip 9 past the cleaning or extractor assembly 7 comprises a moveable shuttle plate 61 mounted for reciprocal sliding movement on the guide rods 62 and 63. The shuttle plate 61 is driven by means of the motor driven cam wheel 64 and the connecting rod 66 pivoted eccentrically to the wheel 64 at pivot point 67 and to the shuttle 61 at pivot point 68. The cam wheel 64 is driven directly by the reduction gear motor 69 mounted on the support 71 carried by the gussets 59. As illustrated in FIG. 2, the cam wheel 64 which is continuously rotated during the intermittent advance of the strip is provided with lobes for operating microswitch 72 as it rotates in order to control the operation of the extractor assembly in conjunction with the advancement of the corrugated strip presently to be described in detail.

The reciprocating slide 61 is provided with a spring biased ratchet dog 73 mounted on the pivot pin 74 carried by the underface of the slide and positioned so as to contact the fluted face of the strip 9 as shown in FIGS. 2 and 3. The dog 73 is urged into contact with the strip 9 by the tension spring 76. The dog has its outer end rounded so as to contact and enter the flutes of the corrugated strip and to advance the strip to the left as viewed in FIGS. 2 and 3 as the slide reciprocates in that direction. The dog is allowed to move freely over the flutes in the opposite direction with the strip being held stationary during the reverse travel of the slide by means of stationary spring biased dog or pawl 77 mounted on the pivot pin 78 carried by the plate 57. The spring 79 biases the pawl 77 in a well known manner such that reverse movement of the strip 9 is prevented as the slide 61 moves in its reverse direction. In this manner, strip 9 is moved in increments past the extractor assembly and cleaning fingers so as to allow the fingers to cycle through their scraping and cleaning motion between increments of movement of the strip. Although a constant pull or tension is maintained on both strips 9 and 11, this pull, because of the slipping engagement between the wheel 28 and the bottom of the turntable 21, is not sufficient to move the strips until the strip 9 is positively advanced by the slide 61.

Referring now to the extractor assembly, the structure is mounted on the upright plate 57 previously mentioned and a second plate 79 spaced therefrom. The extractor assembly includes a motor means, preferably a double acting pneumatic cylinder 81, carried by the plates 57 and 79, which has a piston rod 82 attached to a moveable cross bar 83 guided for vertical reciprocation between the plates 57 and 79. As seen most clearly in FIG. 4, the bar 83 mounts a plurality of first cleaning fingers 84 and a plurality of second opposed cleaning fingers 86. The fingers 84–86 may be made from spring material such as spring steel or any other material which will function to maintain light spring pressure against the opposing flutes of the corrugated strip. In the present embodiment, the opposed sets of fingers may be identical and interchangeable and comprise an upper end 87 held in suitable recesses in the bar 83 by means of the set screws 88, an extended shank portion 84 and an inwardly angled end portion 89 terminating in a curved cleaning tip 91. The recesses in the bar 83 are drilled substantially vertically and the shank portion of the fingers are shaped such that the fingers will normally maintain light spring pressure against the strip 9 with adjustment of the pressure being possible by shaping the shank portion of the fingers and by adjustment of the set screws 88 so as to influence the angle of the shank portion relative to the vertical.

The position of fingers 84 will be offset from that of the fingers 86 in such a fashion that the flutes on both faces of the strip 9 will be cleaned simultaneously as the bar 83 is caused to reciprocate by the air cylinder 81. As shown in FIG. 4, in the extreme raised position of the bar, the sets of fingers ride up onto the sides of the guide bar 48 and are removed from the corrugated strip to permit the strip to be advanced as previously described. The fingers move downwardly off the bar and into contact with the strip to the dotted line position shown to completely scrape each flute and to remove the larva cells therefrom.

Referring to FIGS. 5 and 6, it will be seen that the faces 92 of the tips 91 of the fingers are curved so as to conform to the curvature of the corrugated flutes and have a slight rake angle 92a with respect to the vertical so as to present a leading curved edge 93 to perform an efficient cleaning action.

The electrical and pneumatic control system for operation of the extractor is illustrated in FIG. 8. It will by understood by those skilled in the art, of course, that the details of a suitable electrical control system for operation of the present device may be varied and the presently described control system represents the preferred method of control. Referring to FIG. 1, the electrical controls and control switches may be housed in any suitable control console such as the console 93. FIG. 8 illustrates the first motor 27 for continuously rotating the windup turntable 21 and a second motor 69 which drives the constantly rotating cam wheel 64. The system includes, a master switch 94 providing line power to the system, the takeup motor switch 96, and the cam motor switch 97. As previously described, the pneumatic cylinder 81 which is a double acting cylinder is controlled by the two position air valve 98 which is solenoid operated by means of the solenoid 99 controlled by the micro switch 72 which is in turn operated by the rotating cam wheel 64. A manual override push button switch 101 provides a means for manually operating the fingers through one cycle without operation of the motor 69. Manual operation of the fingers is utilized to cycle the extractor once prior to energizing the advance mechanism when starting a new hive or, for instance, in the case of a malfunction or hangup of the fingers or for testing purposes.

To commence the cleaning of a hive, the spirally wound hive 2 is placed over the spindle or shaft 17 and the separator strip and corrugated strip pulled from the hive a sufficient distance such that the corrugated strip 9 may be advanced through the extractor assembly 7 in position to be grasped by the advancing dogs 73. The separator strip 11 is hand fed around the tension posts 34, 36 and 37 and between the scrapers 39 and 41. The reciprocating shuttle plate at this time will be in its far right hand position as illustrated in FIG. 3 with the microswitch 72 being in its normally open position. At this time, the pushbutton switch 101 may be operated manually to cycle the cleaning fingers to clean the initial portion of the corrugated strip located within the extractor assembly. When the switch 97 is closed, the motor 69 will be actuated to begin rotation of the cam 64 moving the shuttle 61 to the left as shown in FIG. 2 to the end of its stroke. Upon completion of the advance stroke, the cam 64 will be in the position shown in FIG. 2 which will activate the microswitch 72 to operate the solenoid valve 98 to drive the stripper fingers downwardly again to remove cells from the corrugations. The microswitch 72 will remain in its closed position during the return or reverse motion of the shuttle 61 with the holding dogs 77 preventing reverse movement of the corrugated strip during the return stroke. Before the shuttle returns to its initial righthand position the microswitch 72 will ride off the cam 64 causing a retraction of the stripper fingers thus completing one cycle of operation. As the corrugated strip 9 exits the advancing mechanism, it may be manually fed onto the take-up reel 21 along with strip 11 by insertion of the ends of the strips into the slot 26 on the spindle 22. The switch 96 may then be closed so as to activate the motor 27 and the friction drive wheel 28 to maintain a constant tension on both strips as previously described. The cycling of the advance mechanism and stripper fingers continues until the corrugated strip is drawn completely from the hive 2, passed through the extractor, and rewound.

While the present invention has been described with reference to particular embodiments thereof, it will be understood by those skilled in the art that numerous modifications may be made without actually departing from the scope of the invention. Accordingly, all modifications and equivalents may be resorted to which fall within the scope of the invention as claimed.

What is claimed is:

1. Apparatus for cleaning a bee hive which includes a spirally wound strip, the surface thereof having bee larvae adhered thereto comprising in combination:
    means to unwind said strip,
    extractor means operatively associated with said unwinding means for scraping the surface of said strip in a direction transverse to the direction of unwinding of said strip to remove the larvae therefrom, and
    control means for operating said extractor means to scrape the surface of an unwound portion of said strip.

2. The apparatus according to claim 1 wherein:

said strip comprises a corrugated member having bee larvae contained in the flutes thereof, and said extractor means includes a plurality of elongated extractor fingers positioned to simultaneously contact and scrape adjacent flutes of said corrugated strip during operation of the extractor means.

3. The apparatus according to claim 2 wherein:

said elongated extractor fingers are positioned in alternating sequence on opposite sides of said strip to simultaneously contact a plurality of alternately opposite-facing adjacent flutes on opposite sides of said corrugated strip.

4. The apparatus according to claim 3 wherein:

said corrugated strip is maintained and advanced intermittently in predetermined increments in a vertical plane, and said extractor means includes a mounting bar for mounting said plurality of extractor fingers, said bar being located parallel with the plane of said strip, and motor means for vertically reciprocating said bar responsive to said control means to move said fingers through the flutes of said strip.

5. The device according to claim 4 wherein:

said motor means is operative to move said bar and said fingers in a complete cycle from an initial position above and out of contact with said strip, downwardly substantially the width of said strip and back to the initial portion once following each increment of movement of said strip.

6. The apparatus according to claim 5 wherein:

said extractor fingers include means to bias the lower extremities thereof against said strip, and each said lower extremity including a tip portion having a curved leading edge adapted to substantially conform to the curvature of the flutes, the end face of said tip portion being disposed at an acute angle to the surface of the flute, whereby the scraping action of said fingers removes the adherent material from the surface of the associated flute during one cycle of movement thereof.

7. The apparatus according to claim 6 wherein:

said means to unwind said strip includes a reciprocating advance mechanism having an advancing stroke and a return stroke, and motor means for driving said advance mechanism, said advance mechanism including driving pawl means for drivingly contacting the flutes of said strip during the said advancing stroke to move the strip in the advance direction, and holding pawl means for preventing movement of said strip in the opposite direction during said return stroke, whereby said strip is moved in intermittent motion of a predetermined distance.

8. The apparatus according to claim 7, wherein:

said control means includes actuator means responsive to the operation of said advance mechanism to activate the motor of said extractor means to cycle said extractor means once during each return stroke of the advance mechanism, said plurality of extractor fingers being sufficient in number to contact all of the flutes located on the face of the strip over a distance no less than said predetermined distance of incremental movement of said strip.

9. The apparatus according to claim 8 including:

a free spooling unloading reel means for holding said hive to permit unwinding of said strip, a driven take-up reel means for spirally rewinding said corrugated strip subsequent to cleaning thereof by said extractor means, and non positive drive means for said take-up reel to maintain constant tension on said corrugated strip as it is advanced by said advance mechanism.

10. The apparatus according to claim 1 wherein:

said spirally wound strip comprises a first strip having transverse flutes in at least one surface thereof for containing said larvae, and said hive further includes a second spirally wound separator strip in face-to-face relation with said first strip, said apparatus including;

means for unwinding said second strip concurrently with said first strip, means for guiding said first and second strips for movement in separate unwinding paths, and means for scraping the opposed surfaces of said second strip to remove adherent hive material therefrom.

11. The apparatus according to claim 10 including:

a free spooling unloading reel means for holding said hive to permit unwinding of said first and second strips, driven take-up reel means for spirally rewinding said first and second strips in face-to-face relation subsequent to cleaning thereof by said extractor means and said scraping means respectively, and non positive drive means for said take-up reel to maintain constant tension on said first and second strips.

12. The apparatus according to claim 1 including:

a free spooling unloading reel means for holding said hive to permit unwinding of said strip, driven take-up reel means for spirally rewinding said corrugated strip subsequent to cleaning thereof by said extractor means, and non positive drive means for said take-up reel means to maintain constant tension on said corrugated strip.

13. In an apparatus for processing bee larvae cells contained in the cross-fluted surface of an elongated strip including means to advance said strip in intermittent predetermined incremental movement, a larvae extractor comprising:

a plurality of elongated extractor fingers positioned to simultaneously contact and scrape adjacent flutes, a mounting bar for mounting said fingers, and motor means for reciprocating said bar to move said fingers through said flutes following each incremental movement of said strip.

14. The device according to claim 13, wherein said elongated strip comprises a corrugated member having bee larvae contained in the flutes thereof, and said extractor fingers being positioned in alternating sequence on opposite sides of said strip to simultaneously contact a plurality of alternately opposite facing flutes on opposite faces of said strip.

15. The apparatus according to claim 14 wherein:

said corrugated strip is advanced in a vertical plane, and said motor means being adapted to vertically reciprocate said bar to move said fingers in a complete cycle from an initial position above and out of contact with the strip, downwardly substantially the width of said strip and back to the initial position once following each increment of movement of said strip.

16. The apparatus according to claim 15 wherein:
said extractor fingers include means to bias the lower extremities thereof against said strip, and
each said lower extremity including a tip portion having a curved leading edge adapted to substantially conform to the curvature of the flutes, the end face of said tip portion being disposed at an acute angle to the surface of the flute,
whereby the scraping action of said fingers removes the adherent material from the surface of the associated flute during one cycle of movement thereof.

17. A method for cleaning a bee hive composed of a spirally wound strip, the surface thereof having bee larvae adhered thereto comprising the steps of:
unwinding said strip to expose the larvae cells on the surface thereof,
scraping the surface of an unwound portion of said strip in a direction transverse to the direction of unwinding of said strip to remove the larvae therefrom; and
spirally rewinding said strip to reform said spiral hive.

18. The method according to claim 17 wherein:
said strip comprises a first cross fluted member and said bee hive includes a second separator strip in face-to-face relation with said first strip, the method including the steps of:
moving said first and second strips along separate paths,
scraping the opposed surfaces of said second strip to remove hive material adhering thereto, and
bringing said first and second strips back into face-to-face relation prior to spirally rewinding both strips to reform said hive.

19. The method according to claim 18 wherein said first strip comprises a corrugated member and wherein said unwinding proceeds intermittently in predetermined increments, the method including the step of:
simultaneously scraping the alternately opposite-facing flutes on both opposed surfaces of said corrugated member along a length of the member no less than the distance of each increment of intermittent movement thereof.

* * * * *

UNITED STATES PATENT AND TRADEMARK OFFICE
CERTIFICATE OF CORRECTION

PATENT NO. : 4,293,966
DATED : October 13, 1981
INVENTOR(S) : LeRoy J. Wiederrich It is certified that error appears in the above-identified patent and that said Letters Patent are hereby corrected as shown below:

Col. 1, line 39, after "has" insert --not--.

Signed and Sealed this

Twenty-ninth Day of December 1981

[SEAL]

Attest:

GERALD J. MOSSINGHOFF

Attesting Officer                Commissioner of Patents and Trademarks